United States Patent
Karch et al.

(10) Patent No.: US 7,309,679 B2
(45) Date of Patent: Dec. 18, 2007

(54) ATTRITION RESISTANT MTO CATALYST

(75) Inventors: John A. Karch, Lake Zurich, IL (US); Thomas M. Reynolds, Mobile, AL (US)

(73) Assignee: UOP LLC, Des Plaines, IL (US)

( * ) Notice: Subject to any disclaimer, the term of this patent is extended or adjusted under 35 U.S.C. 154(b) by 201 days.

(21) Appl. No.: 11/199,347

(22) Filed: Aug. 8, 2005

(65) Prior Publication Data

US 2007/0032378 A1 Feb. 8, 2007

(51) Int. Cl.
*B01J 27/182* (2006.01)
(52) U.S. Cl. ...................... 502/214; 502/208
(58) Field of Classification Search ................ 502/208, 502/214
See application file for complete search history.

(56) References Cited

U.S. PATENT DOCUMENTS

| | | | |
|---|---|---|---|
| 3,957,689 A | 5/1976 | Ostermaier et al. | 252/455 Z |
| 4,440,871 A | 4/1984 | Lok et al. | 502/214 |
| 4,987,110 A | 1/1991 | Scherzer | 502/68 |
| 5,135,756 A * | 8/1992 | Shi et al. | 502/62 |
| 5,168,086 A * | 12/1992 | Cheng et al. | 502/66 |
| 5,248,647 A | 9/1993 | Barger | 502/214 |
| 5,286,369 A * | 2/1994 | Roberie et al. | 208/114 |
| 5,352,645 A | 10/1994 | Schwartz | 502/262 |
| 5,739,072 A * | 4/1998 | Shi et al. | 502/72 |
| 5,866,496 A * | 2/1999 | Albers et al. | 502/68 |
| 6,153,552 A * | 11/2000 | Wachter et al. | 502/208 |
| 6,362,128 B1 | 3/2002 | Schwartz | 502/209 |
| 6,589,902 B1 | 7/2003 | Stamires et al. | 502/80 |
| 6,878,668 B1 | 4/2005 | Schwartz et al. | 502/247 |
| 2002/0165090 A1 | 11/2002 | Janssen et al. | 502/214 |

FOREIGN PATENT DOCUMENTS

| | | |
|---|---|---|
| EP | 0558839 | 8/1993 |
| WO | WO 9921653 | 5/1999 |
| WO | WO 02/05952 | 1/2002 |
| WO | WO 03000413 | 1/2003 |
| WO | WO 2004/060559 | 7/2004 |
| WO | WO 2005025744 | 3/2005 |

\* cited by examiner

*Primary Examiner*—Elizabeth D. Wood
(74) *Attorney, Agent, or Firm*—Arthur E Gooding

(57) ABSTRACT

A process is presented for the formation of a SAPO-34 catalyst product. The process creates a harder, more attrition resistant catalyst for use in the MTO process.

10 Claims, No Drawings

US 7,309,679 B2

ATTRITION RESISTANT MTO CATALYST

FIELD OF THE INVENTION

The present invention relates to a process for producing a catalyst for converting oxygenates to olefins. The process produces a catalyst with greater attrition resistance.

BACKGROUND OF THE INVENTION

Light olefins are an important basic chemical feedstock for the production of many plastics used in a variety of industries. Olefins are most commonly produced from petroleum feedstocks through the cracking of larger hydrocarbon molecules. The cracking process is either a catalytic or steam cracking process, and produces light olefins which consist primarily of ethylene and propylene.

An alternate source of light olefins is from the conversion of oxygenates to olefins. The primary oxygenate that is converted to an olefin is methanol. The preferred process is generally referred to as methanol-to-olefins (MTO) process. The primary olefins produced from this process are ethylene and propylene, and the process is performed over a catalytic molecular sieve. The MTO process enables an important alternative to petroleum sources of feeds for the production of light olefins. The sources of oxygenates include alcohols, such as methanol and ethanol; ethers, such as dimethyl ether and diethyl ether; and other oxygenates, such as methyl formate and dimethyl carbonate. These oxygenates can be produced from natural gas, fermentation of biomass, municipal wastes, and recycled organic materials. An important commercial consideration is that methanol can be readily produced from natural gas, or coal, and is easier and safer to handle and transport then either natural gas or coal.

There are numerous patents describing improved preparation of zeolites. U.S. Pat. No. 3,957,689 describes a process for making attrition resistant faujasite zeolites. U.S. Pat. No. 4,987,110 describes a process for making attrition resistant molecular sieves by adding a clay and aluminum chlorhydroxide. U.S. Pat. No. 5,352,645 describes a process for producing hardened silica microspheres. U.S. Pat. No. 6,362,128 describes a process for producing catalysts having oxide-rich outer layers with improved attrition resistance. U.S. Pat. No. 6,589,902 describes a process for producing attrition resistant materials containing crystalline anionic clays and U.S. Pat. No. 6,878,668 describes a process for producing attrition resistant vanadium/phosphorous oxide catalyst. In view of the above prior art, it can be seen that the type of molecular sieve or catalyst, composition, size, and processing conditions affect the process of producing attrition resistant particles, and requires significant experimentation without providing guidance for specific molecular sieves.

The environment for the production of methanol to olefins, i.e. the reactor, is a severe physical environment. The reactor is generally a fluidized bed, and the catalyst particles are subject to constant rubbing against other particles and the reactor walls, as well as physical contact with other equipment. This tends to break down the catalyst particles, causing fines which need to be removed from the system, as well as shortening the life of the catalyst particles. It would be useful to produce a catalyst that is more attrition resistant, and therefore has a longer, more economical life.

SUMMARY OF THE INVENTION

The present invention provides an attrition resistant catalyst. The catalyst is for use in the MTO process in an environment that is physically damaging to the catalyst. The catalyst comprises a molecular sieve which is crystallized from a reaction mixture comprising aluminum, phosphorus, a metal, water, and an organic template. After crystallization, the molecular sieve is washed, then the washed molecular sieve is mixed with a sodium silicate and an acid alum to form a catalyst slurry. The catalyst slurry is spray dried to form hard particles of the catalyst.

Additional objects, embodiments and details of this invention can be obtained from the following detailed description of the invention.

DETAILED DESCRIPTION OF THE INVENTION

An attrition resistant catalyst is important for use in physically demanding environments. Of particular concern are environments such as fluidized beds where the catalyst is continuously tumbled and abrades against other catalyst particles and against the walls of the reactor. One particular catalyst of interest, a SAPO-34 catalyst, is a catalyst for the methanol to olefin conversion process.

The SAPO-34 molecular sieve belongs to the family of molecular sieves having the structure type of the zeolitic mineral chabazite (CHA). The preparation and characterization of SAPO-34 is known in the art, as exemplified in U.S. Pat. Nos. 4,440,871; 5,248,647 and US 2002/0165090 A1, which are incorporated by reference in their entireties.

The preparation of a SAPO-34 molecular sieve comprises providing a reaction mixture including aluminum, phosphorus, water, an organic template and silicon. This preparation is applicable more broadly to ElAPO molecular sieves, where the element, El is chosen to be one or more elements from silicon, magnesium, zinc, iron, cobalt, nickel, manganese and chromium. The resulting catalyst has a chemical composition on an anhydrous basis expressed by an empirical formula of:

$$(El_xAl_yP_z)O_2$$

The "x" is the mole fraction of El and has a value of at least 0.001, "y" is the mole fraction of Al and has a value of at least 0.01, and "z" is the mole fraction of P and has a value of at least 0.01. The sum of x, y and z equals 1, or x+y+z=1.

Organic templating agents include amines, and quaternary ammonium compounds. Examples of templating agents include, but are not limited to morpholine, tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium fluoride, tetraethyl ammonium acetate, dipropylamine (DPA), isopropylamine, cyclohexylamine, methylbutylamine, diethanolamine, morpholine, diethylethanolamine, N-methylethanolamine, tetramethylammonium hydroxide, sec-butylamine, dimethylethanolamine, N-methyl-butylamine, methyldiethanolamine, 2,2-dimethyl-1,3-propanediamine, cyclohexylamine, triethylamine, N,N,N',N'-tetramethyl-ethylenediamine, diisopropylamine, N-ethyl-butylamine, 2-methyl-1,5-pentanediamine, N,N-dimethylbutylamine, N,N,N',N'-tetramethyl-1,3-butanediamine, N,N,N',N'-tetramethyl-1,4-butanediamine, N,N-dimethylcyclohexylamine, N,N-dimethyl-benzylamine, C,C,C-trimethyl-1,6-hexanediamine, N,N,N',N'-tetraethyl-ethylenediamine, 4-piperidino-piperidine, N,N,N',N'-tetraethyl-1,3-propane-diamine, tetrapropylammonium hydroxide, N,N,N',N'-tetraethyl-diethylenetriamine and 1,1'-methylene-bis(3-methylpiperidine).

Crystallization of the reaction mixture at a temperature from 100° C. to 250° C. produces a molecular sieve. The resulting molecular sieve crystals are then washed. The normal processing of molecular sieve involves drying the molecular sieve. This, however, tends to agglomerate the crystals. It has been found that instead of drying the crystals after formation, harder, more attrition resistant crystals can be formed through a new process.

After washing the molecular sieve, a slurry with the molecular sieve crystals is formed without drying to maintain a small crystal size, adding a sodium silicate and acid alum to the slurry. The slurry is mixed in a high shear mixer and spray dried, producing small particles of catalyst product that are much harder and more attrition resistant. The mixing time should be short to avoid the binder gelling, and should be between about 10 seconds and about 60 minutes. The time for mixing is subject to the amount of shear provided by the mixer and other operating considerations.

As an alternative, the molecular sieve can remain unwashed using a slurry of unwashed molecular sieve with sodium silicate and acid alum. Spray drying will allow for vaporization of residual organic template. It is believed that the remaining dissolved oxides will contribute to the product strength.

The acid alum is a mixture of aluminum sulfate and sulfuric acid. Sodium silicate is a solution of silica dissolved in a caustic material, with a typical ratio of silica to caustic of about 3:1 by weight. When the acid alum and sodium silicate are mixed, the resulting solution is acidified waterglass. The two solutions are mixed in a ratio that produces a waterglass with a pH from about 2-3.

Additional binders which can be added to the slurry include, but are not limited to, aluminas, silicas, silica-alumina, aluminum phosphate, titania and zirconia. Other inorganic binders are also usable in this process and include for example magnesia, chromia, boria, thoria, and zinc oxides. The binders can also be added as a colloidal sol comprising silica, alumina, or silica-alumina. It should be noted that the term silica-alumina does not mean a physical mixture of silica and alumina but means an acidic and amorphous material that has been cogelled or coprecipitated. In this respect, it is possible to form other cogelled or coprecipitated amorphous materials that will also be effective as binders. These include silica-magnesias, silica-zirconias, silica-thorias, silica-berylias, silica-titanias, silica-alumina-thorias, silica-alumina-zirconias, aluminophosphates, mixtures of these, and the like.

When forming the catalyst product, the molecular sieve has a composition between about 15 weight % and about 50 weight % of the dried catalyst product. The binder in the catalyst product forms between 10 weight % and about 90 weight % of the dried catalyst product.

It is preferred to optionally add a clay to the catalyst. The clay is added to the catalyst slurry before the mixing of the molecular sieve and binder, and the resultant slurry is mixed and spray dried. When adding clay, the clay forms between about 40 weight % and about 80 weight % of the dried catalyst product. Clays that are used in this process to form a hardened product include, but are not limited to, kaolin, kaolinite, montmorillonite, saponite, bentonite, attapulgite and halloysite.

Clays contribute strength as a binder enhancing the attrition resistance properties of the catalyst particles, and clays in combination with binders contribute to the hardness of the particles. Clays also start as small particles and have a higher density, such that when combined with the molecular sieve and binder provide for denser particles, imparting the desirable characteristic of higher density.

The catalyst's attrition was determined using a standard FCC attrition test as shown in Katalistiks attrition test procedure. This procedure is very similar to the ASTM-attrition test. The test comprises drying a sample, and mixing the sample with water to bring the sample to a constant moisture level. In this procedure the sample is dried at 500° C., and then 45 g of sample is mixed with 5 g of water. The sample is loaded into a chamber that has three jeweled orifices. Air is blown through the orifices to fluidize the bed. The fines generated are collected in a porous thimble at 1, 3 and 5 hours, and then weighed. The losses are calculated in percent weight loss per hours, or as an attrition index of Ks. The units are the slope of the line generated from regression analysis. If the correlation coefficient is less than 0.99, then the data is suspect and a new test needs to be run.

The following examples are presented to more fully illustrate embodiments of the invention, and are not intended to limit the scope of the invention as set forth in the appended claims.

EXAMPLE 1

A SAPO-34 molecular sieve was produced as set forth in U.S. Pat. No. 4,440,871. The net SAPO-34 product was mixed with an acidified waterglass and clay forming a slurry of molecular sieve, binder and clay having a 31.6 weight % solids content. This slurry comprised, on a dry basis, SAPO-34 molecular sieve at 20 wt. %, silica/alumina binder at 20 wt. %, and kaolin clay at 60 wt. %. The slurry was mixed for about two minutes, and then spray dried forming a catalyst product. The catalyst product was washed using a standard wash comprising water and ammonium nitrate to remove each of sodium and sulfate to less than 0.1 wt. %. The washed molecular sieve product was calcined in a laboratory furnace at 650° C. The catalyst produced through this process had an attrition level of about 0.025 attrition units (Ks value), or in percent weight loss per hour.

EXAMPLE 2

In another test, the MTO catalyst product comprising SAPO-34 molecular sieve at 20 wt. %, silica/alumina binder at 20 wt. %, and kaolin clay at 60 wt. % was mixed in a slurry, and then spray dried to form particles. The resulting catalyst product was determined to have an attrition level from about 0.1 to 0.2 (Ks).

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A method of making a catalyst for use in the process of converting oxygenates to olefins comprising:

providing a reaction mixture comprising aluminum, phosphorus, water, an organic template and an element selected from the group consisting of silicon, magnesium, zinc, iron, cobalt, nickel, manganese, chromium, and mixtures thereof, to form a non-zeolitic molecular sieve having a chemical composition on an anhydrous basis expressed by an empirical formula of:

$$(El_xAl_yP_z)O_2$$

wherein "x" is the mole fraction of El and has a value of at least 0.001, "y" is the mole fraction of Al and has a value of at least 0.01, "z" is the mole fraction of P and has a value of at least 0.01 and x+y+z=1, crystallizing the molecular sieves at a temperature between about 100° C. and about 250 °C.; and washing the molecular sieve, without drying the molecular sieve;

adding a first binder comprising sodium silicate and acid alum to the washed molecular sieve to form a catalyst slurry;

spray drying the catalyst slurry, and calcining at a temperature greater than 500° C. to form an attrition resistant catalyst.

2. The method of claim 1 wherein the slurry is mixed for a time of about 10 seconds to about 60 minutes.

3. The method of claim 1 further comprising adding a second binder to the slurry.

4. The method of claim 3 wherein the second binder is selected from the group consisting of silica, aluminas, silica-alumina, aluminum phosphate, titania, zirconia and mixtures thereof.

5. The method of claim 3 wherein the second binder comprises between 10 weight % and 90 weight % of the dried catalyst product.

6. The method of claim 3 wherein the molecular sieve comprises between 15 weight % and 50 weight % of the dried catalyst product.

7. The method of claim 1 further comprising adding a clay to the slurry.

8. The method of claim 7 wherein the clay comprises between 40 weight % to 80 weight % of the dried molecular sieve product.

9. The method of claim 7 wherein the clay is selected from the group consisting of kaolin, kaolinite, montmorillonite, saponite, bentonite, attapulgite, halloysite and mixtures thereof.

10. The method of claim 1 wherein the organic template is selected from the group consisting of tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium fluoride, tetraethyl ammonium acetate, dipropylamine (DPA), isopropylamine, cyclohexylamine, methylbutylamine, diethanolamine, morpholine, diethylethanolamine, N-methylethanolamine, tetramethylammonium hydroxide, sec-butylamine, dimethylethanolamine, N-methyl-butylamine, methyldiethanolamine, 2,2-dimethyl-1,3-propanediamine, cyclohexylamine, triethylamine, N,N,N',N'-tetramethyl-ethylenediamine, diisopropylamine, N-ethyl-butylamine, 2-methyl-1,5-pentanediamine, N,N-dimethylbutylamine, N,N,N',N'-tetramethyl-1,3-butanediamine, N,N,N',N'-tetramethyl-1,4-butanediamine, N,N-dimethylcyclohexylamine, N,N-dimethyl-benzylamine, C,C,C-trimethyl-1,6-hexanediamine, N,N,N',N'-tetraethyl-ethylenediamine, 4-piperidino-piperidine, N,N,N',N'-tetraethyl-1,3-propane-diamine, tetrapropylammonium hydroxide, N,N,N',N'-tetraethyl-diethylenetriamine, 1,1'-methylene-bis(3-methylpiperidine) and mixtures thereof.

* * * * *